United States Patent [19]

Ringrose

[11] 4,149,405
[45] Apr. 17, 1979

[54] PROCESS FOR MEASURING THE VISCOSITY OF A FLUID SUBSTANCE

[75] Inventor: Anthony Ringrose, Chene-Bougeries, Switzerland

[73] Assignee: Battelle, Centre de Recherche de Geneve, Carouge, Switzerland

[21] Appl. No.: 867,878

[22] Filed: Jan. 9, 1978

[30] Foreign Application Priority Data

Jan. 10, 1977 [CH] Switzerland ............................ 226/77

[51] Int. Cl.² .......................................... G01N 11/00
[52] U.S. Cl. ........................................ 73/54; 73/64.1; 356/39
[58] Field of Search ................. 73/54, 59, 64.1, 17 R; 356/39, 196, 197; 23/230 B

[56] References Cited

U.S. PATENT DOCUMENTS

| | | | |
|---|---|---|---|
| 3,077,764 | 2/1963 | Kapff | 73/54 X |
| 3,650,698 | 3/1972 | Adler | 356/39 X |
| 3,752,443 | 8/1973 | Lichtenstein | 356/39 X |

*Primary Examiner*—Richard C. Queisser
*Assistant Examiner*—Joseph W. Roskos
*Attorney, Agent, or Firm*—Karl F. Ross

[57] ABSTRACT

The viscosity of a fluid material, e.g. a synthetic-resin composition, or the coagulation of blood or plasma monitored by placing a quantity of the fluid substance on a support, directing a beam of light upon the sample, detecting reflected light from the sample and vibrating the support at a given frequency and amplitude to disturb its surface. The reflected light detected is a function of the viscosity or the degree of coagulation.

6 Claims, 6 Drawing Figures

PROCESS FOR MEASURING THE VISCOSITY OF A FLUID SUBSTANCE

FIELD OF THE INVENTION

The present invention relates to the determination of the viscosity of a fluid material and, more particularly, to a method of and a device for determining the viscosity of fluid materials or the coagulation of blood or blood plasma.

BACKGROUND OF THE INVENTION

In order to measure the viscosity of a fluid substance a certain deformation force can be exerted on this substance and the resistance offered by the substance can be measured. Although blood coagulation is not strictly speaking a viscosity, its measurement can be closely paralleled with that of a viscosity measurement in that a sample is subjected to a particular deformation force and the deformation is observed.

Blood coagulation is the result of a particularly complex biochemical process which is caused according to the type by different combinations of a plurality of components called "factors" contained in the blood. At the present twelve factors are said to play a role in this process.

Interactions between these factors lead in the case of normal blood to the formation of a filamentary network called fibrin, the production of which is characteristic of coagulation. The purpose of the coagulometer is to detect the exact instant of the formation of this network.

The coagulation of blood in the laboratory has been initiated heretofore by several different methods each relying on the use of a respective different group of factors as a function of the information desired. The choice of methods allows one to eliminate or to accentuate the action of different factors in the blood. The sample is either whole blood or plasma. In most cases this blood or this plasma is prevented from coagulating by the addition of an anticoagulant to the fresh blood, this anticoagulant being constituted by a solution of trisodium citrate or sodium oxalate. The plasmas of blood treated with one or the other of these solutions is called "citrated plasma" or "oxalated plasma". These solutions have the effect of eliminating $Ca^{++}$ ions from the blood, following which the plasma is separated by centrifuging.

Most coagulometers in use read out the time of incipient appearance of the fibrin. There is a wide variety of electromechanical measuring devices for coagulation in use in laboratories. Many of these devices are rather imprecise and disturb the blood during the coagulation process. Most require a relatively large quantity of blood as the sample and only measure a single point in the coagulation process, not allowing one to measure the evolution of this process. As a rule these devices cannot be used for all coagulation measurements.

Although in many cases the numerical measurement of the process is sufficient, for example for monitoring the administration of anticoagulant substances, it is occasionally useful to know more about the entire evolution of the process, for instance to advance research in this field and to allow more precise diagnoses.

There are so-called "thromboelastographs" which record coagulation graphs. As a result of their complexity such devices cannot be used for running analyses.

The very newest devices meant for use in analytic laboratories are photometric devices which measure the absorption by the sample of a light beam. The formation of fibrin, which is characteristic of coagulation, increasingly diffuses the light of the beam. The remaining light, and as a result the absorbance of the sample, is measured by a photoelectric cell placed across from the source of light, this cell and this source being to opposite sides of the sample.

This analysis system has two advantages over those which have existed to date. No object touches the sample during analysis, and the signal picked up is analog and usable for drawing a graph indicating the evolution of the process.

Nonetheless the basic principle on which this apparatus operates is incompatible with certain analytical methods or for certain pathogenic forms of plasma or blood. The analysis of whole blood is effectively ruled out by the fact that such blood is too opaque. This detection method is in addition poorly adapted for measuring the coagulation of exalted plasmas because they are disturbed during the process. For certain diseases, lipemia for example, the plasma is cloudy, thereby falsifying the measurement. Finally the evaluation of the formation of fibrin is very temporary with such a device.

There are fields other than hematology wherein the measurement of viscosity itself sometimes poses problems that are only inadequately solved, in particular measurement of the viscosity of non-Newtonian liquids. As is known this viscosity is mainly a function of the speed of deformation of these liquids. As a result their measurement can only be made by applying different deformation speeds at a constant temperature so that the viscosity is a curve illustrating a function of these speeds of deformation. In any case the known viscosimeters hardly allow one to measure viscosities at deformation speeds less than $1\ sec^{-1}$. On the other hand the determination of the viscosity at a very small deformation speed is of interest because it allows one to determine a molecular weight of a polymer.

OBJECT OF THE INVENTION

An object of the present invention is to overcome at least in part the above-given disadvantages.

SUMMARY OF THE INVENTION

The above and other objects are attained, in accordance with the invention, in a process for measuring the viscosity of a fluid substance, in particular the evolution of blood coagulation, as a function of time, in that a sample to be measured is placed on a support, a beam of light is directed against the free surface of this sample, the sample is vibrated at a given frequency and amplitude so as to disturb its free surface and the light reflected by a portion of this surface, which is characteristic of the viscosity of this sample, is measured.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
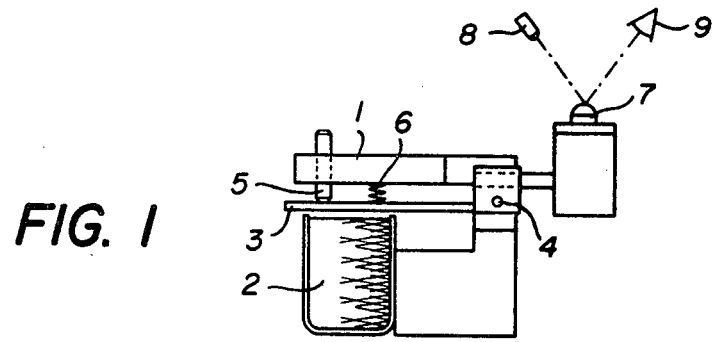
FIG. 1 is a side-elevational view of an apparatus for carrying out the method of the present invention.

The apparatus of FIG. 1 comprises a support 1 carrying an electromagnet 2 and an arm 3 pivoted about an axle 4 and whose degree of motion is determined by an abutment 5 spaced from the electromagnet 2. A return spring 6 biases the arm 3 against the abutment 5. This arm 3 carries a plate 7 adapted to carry the sample. Preferably this plate is formed of a synthetic-resin material such as Delrin rather than glass whose influence on the coagulation process is known.

A light source 8 is aimed at the center of the plate and a photoelectric receiver 9 is placed at a location determined by the reflected light. As will be seen below when the arm 3 is at rest, the receiver 9 can either receive the light reflected from the surface of the sample carried by the plate 7 or receive no light.

The principle on which the method is based consists of forming on the plate 7 a drop of the sample calibrated in such a manner that its shape can be reproduced. This sample is either formed of whole blood or of plasmas and an appropriate reagent. When the sample is placed on the plate, this plate is vibrated and the surface of the drop is irradicated. The vibrations which deform the surface of this drop disturb the light reflected by this surface. As soon as coagulation starts the influence of the vibrations on the surface of this drop diminish progressively so that the amount of reflected light received by the receiver 9 varies until the coagulation is complete. If the receiver 9 is normally positioned in the path of the beam of reflected light the quantity of light received will vary from a minimum to a maximum between the start and the end of the process period. However if the receiver 9 is normally outside of this path, the vibrations communicated to the drop of the sample before coagulation make the deformed surface of this drop reflect a part of the light toward the cell 9 and this quantity will decrease as the coagulation reduces the extent of the deformations transmitted to the surface of the drop.

In the arrangement shown in FIG. 1 the vibrations are caused by the electromagnet 2 fed by current pulses at a frequency from 2-4 Hz. These pulses vibrate the arm 3 urged by the spring 6 between the electromagnet 2 and the abutment 5.

Figure 2:
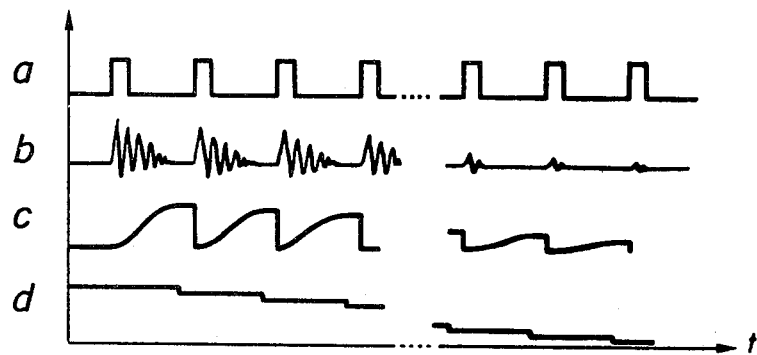
FIG. 2 is a diagram illustrating the functioning of the apparatus and the treatment of the signal obtained.
Figure 3:
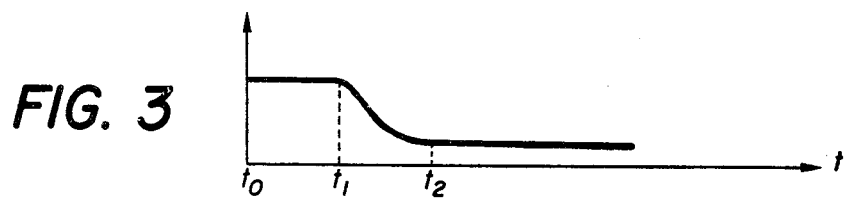
FIGS. 3–5 are three graphs of tests of coagulation of three different samples.

Different tests have been carried out with the aid of equipment similar to that illustrated in FIG. 1 by treating the detected signals from the receiver 9 as shown in FIG. 2. In this diagram four series of signals a, b, c and d are shown. The signals a represent the feed pulses for the magnet 2, the signals b correspond to the excitation current of the photoelectric receiver 9 caused by the light received from a reflection of the light incident against the surface of the drop of the sample being vibrated as the electromagnet is excited. This current is proportional to the light received by the receiver and is as a result a function of the deformation of the surface of the drop of the sample being vibrated. The signal c corresponds to the integral of the signal b. The signal d corresponds to the value of the peaks of the signal c and is used for forming the curves of FIGS. 3-5.

The tests carried out to evaluate the performance of this method consist in measuring the time of prothrombin of a citrated control sample sold commercially and whose normal prothrombin time is known.

In order to measure the coagulation with this method the plasma is heated to 37° C. 30 $\mu l$ are pipetted onto the plate 7 also heated to 37° C. Then on this same plate 60 $\mu l$ of a reagent are deposited, normally a solution of thromboplastine and calcium chloride which has been heated to 37° C. The addition of this reagent determines very exactly the time $t_0$ corresponding to the start of measurement and to the start of the excitation of the electromagnet 2 by the train of pulses a (FIG. 2) which vibrates the plate 7. The signal treated as described above is fed to a recording instrument which traces a curve similar to that of FIG. 3. On this curve the prothrombin time is given by $t_1$ which corresponds to the beginning of the formation of fibrin. Most of prior-art devices only allow determination of this time $t_1$. The process according to the invention allows in addition the following of the evolution of the coagulation process until its end.

Figure 4:
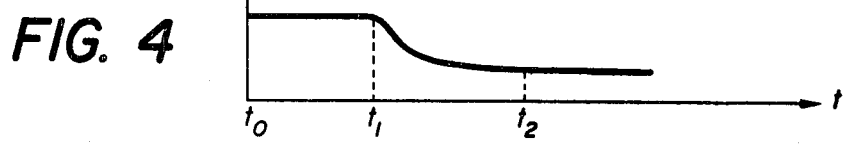
Figure 5:
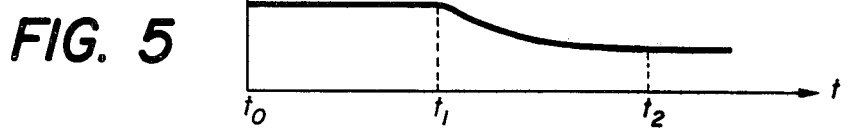

The diagram of FIGS. 4 and 5 show the use of this graphic analytical method for the coagulation process. The traph of FIG. 4 was traced by using the same control plasma as mentioned above, but diluted to 50% of artificial serum, whereas the graph of FIG. 4 corresponds to this same control plasma diluted to 75% of artificial serum. It can be seen that in these two cases not only does the time $t_1$ vary as a function of the dilution of the plasma, but that the shape of the curve between $t_1$ and $t_2$ is very different. This shows that the process of the invention allows the detection in addition to the prothrombine time of the complete coagulation time which itself varies noticeably as a function of the density of the fibrin network which forms not only at its start but also during the process. It is of course possible to observe the process of coagulation by introducing other "factors" than the method described. In all these cases the same mechanical phenomena would produce the same effects independent of the intervening factors in the coagulation process.

In addition to certain advantages of the process already mentioned it is also important to point out that the plasma is subjected to minimal disturbances during the coagulation process. The detecting devices of the process do not contact the substance which is reacting. The measuring process according to the invention is usable for all known methods no matter what the nature of the sample to be analyzed. In the tests tried the quantity of the sample is particularly small. At the same time nothing prevents it from being reduced further, the critical problem then being only that of the precision of the pipetting. The results obtained can be given either in numerical form or in analog form or even in both of these forms. The apparatus necessary for carrying out the process is extremely simple.

In addition to measuring the evolution of sanguine coagulation, the process described above is also in interest for the measurement of the viscosity of non-Newtonian liquids. It is not considered possible to measure the viscosity for deformation speeds smaller than 1 $sec^{-1}$ with known viscosimeters. Knowing the viscosity at small deformation speeds would, however, be important because it would allow one to determine the molecular weight of a polymer.

Figure 6:
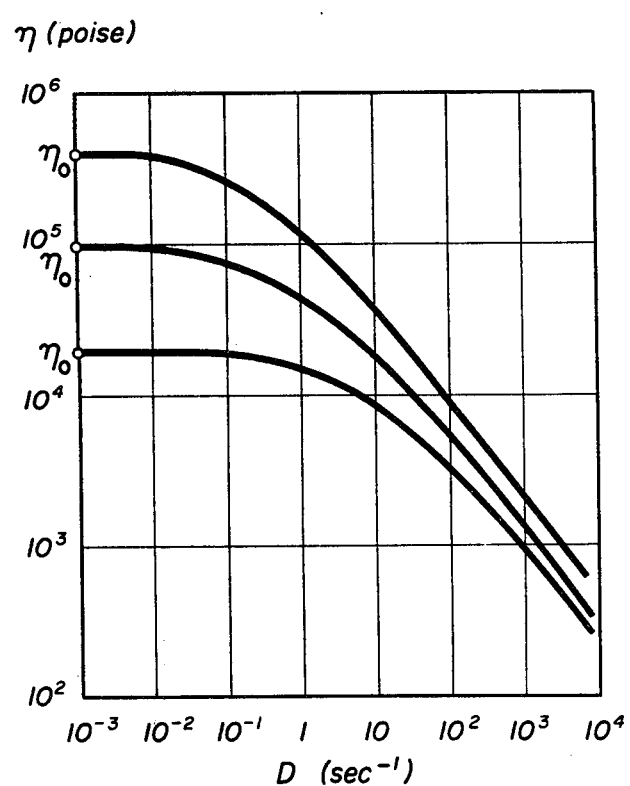
FIG. 6 is a graph showing the viscosity of a polymer as a function of the deformation speed which is applied to it.

The process, according to the invention, produces an output which is a function of the forces dissipated in the liquid and, therefore, of its viscosity. The vibration to which the sample is subjected allows one to communicate to it a very small deformation speed. As seen in FIG. 6 which shows the viscosity curves of three polyethylenes it is possible to note that as the deformation speed D goes to zero the measured viscosity $\eta$ corresponds practically to $\eta_o$. This means that it is possible with the process, according to the invention, to measure the viscosity $\eta_o$ of a polymer.

I claim:

1. A process for measuring the viscosity of a fluid substance comprising the steps of:

placing a sample of the fluid substance whose viscosity is to be measured upon a support;

training a beam of light upon the sample on said support;

vibrating said support with said sample thereon to disturb the surface of the sample; and measuring light reflected from said support, the measured reflected light being a function of the viscosity of said sample.

2. The process defined in claim 1 wherein the reflectivity from said sample is measured as a function of time to monitor the change in viscosity of said sample over a time period.

3. The process defined in claim 2 wherein said sample is a synthetic resin.

4. The process defined in claim 2 wherein said sample includes coagulatable blood components, the change in viscosity of said sample being a function of the coagulation of said component.

5. A process for detecting the coagulation of blood components in a fluid substance, said process comprising the steps of:

placing a sample of said fluid substance on a support;

training a beam of light on said sample on said support;

vibrating said sample to disturb the surface thereof at a predetermined frequency and amplitude;

measuring reflected light from said surface as a function of time; and establishing as the coagulation time of said sample the period of onset of measurement of the reflected light to incipient decrease in the amplitude of the light reflected from said surface.

6. The process defined in claim 5, further comprising monitoring the evolution of coagulation subsequent to said coagulation time by continuing to monitor reflected light from said surface after said coagulation time.

* * * * *